United States Patent [19]
Juhasz

[11] Patent Number: 5,061,251
[45] Date of Patent: Oct. 29, 1991

[54] SYRINGE DEVICE
[76] Inventor: Paul R. Juhasz, P.O. Box 1013, Columbia, Md. 21044
[21] Appl. No.: 537,085
[22] Filed: Jun. 12, 1990
[51] Int. Cl.[5] ............................................... A61M 5/00
[52] U.S. Cl. ..................................... 604/198; 604/263
[58] Field of Search ................ 604/198, 263, 187, 192

[56] References Cited
U.S. PATENT DOCUMENTS

| | | | |
|---|---|---|---|
| 4,639,249 | 1/1987 | Larson | 604/198 |
| 4,927,416 | 5/1990 | Tomkiel | 604/263 |
| 4,932,940 | 6/1990 | Walker et al. | 604/198 |
| 4,932,947 | 6/1990 | Cardwell | 604/198 |
| 4,966,592 | 10/1990 | Burns et al. | 604/198 |

Primary Examiner—John D. Yasko

[57] ABSTRACT

So as to prevent accidental needle contacts when a syringe device is not being used, I have devised a syringe device in which I have made a movable shield member, integral with a syringe member of said device, to be movably interconnected with the syringe member for movement between a first position for shielding a needle member of said device and a second position for exposing the needle member, I have provided means for manually moving the shield member from the first to the second position, and I have disposed between the shield member and the syringe member, spring means for normally biasing the shield member in the shielding position when the syringe device is not being used.

13 Claims, 1 Drawing Sheet

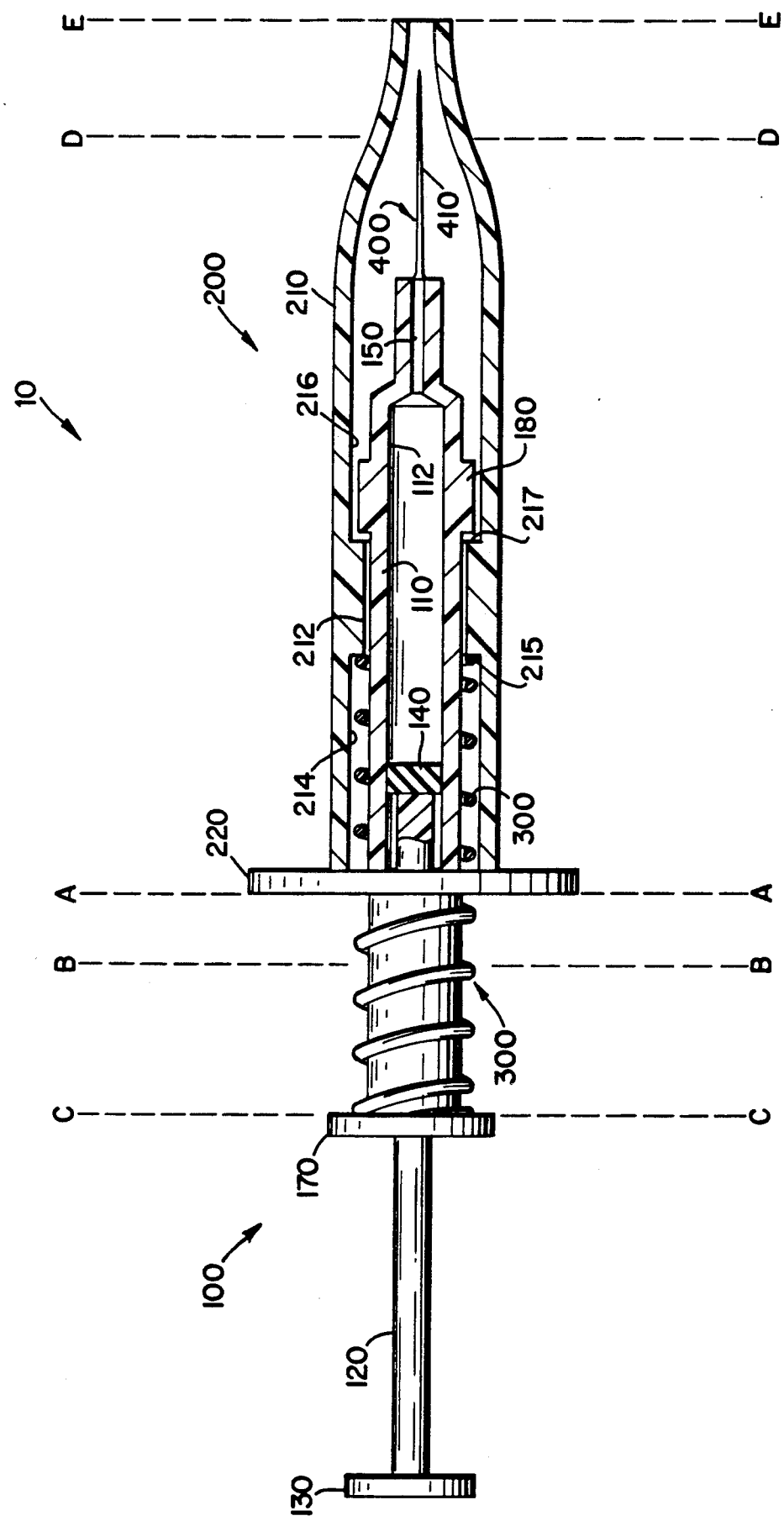

SYRINGE DEVICE

BACKGROUND OF THE INVENTION

This invention relates generally to syringe devices and particularly to syringe devices that are adapted to shielding a hypodermic needle attached thereto so as to prevent accidental needle contact when the syringe device is not being used.

Health care and other individuals who work in proximity to hypodermic needle type syringe devices are susceptible to accidental and potentially infectious contact with hypodermic needles attached thereto due to careless handling and disposing of the syringe devices after being used.

Several techniques have been proposed in an effort to prevent such accidental needle contacts. In a first technique, advanced in U.S. Pat. Nos. 4,735,618 and 4,139,009, a needle cap or needle assembly component, respectfully, of a syringe device is provided with a shield which collapses upon itself in the syringe direction as the needle end of the shield is pressed against the skin surface (or vial surface) where the injection (or fluid withdrawal) is to be made. A needle assembly component also operating on this principle but for the objective of making the needle hidden at all times from patient view is described in U.S. Pat. No. 3,134,380. However, the technique in these patents not only requires the circumference of the shield to be pressed against the injection surface for the shield to collapse. Thus, if an insufficient area of contact is available or there is an improper alignment of circumference of shield with area of contact then the shield may not properly collapse. But the shield must also stay pressed against the injection surface for the shield to stay collapsed. Thus, during an injection, for example, the needle is at all times, including as it penetrates the patient, completely obstructed from view by the shield, making accurate positioning of the needle against the skin of the patient difficult. In addition, resistance to collapsing of the shield places a positive pressure on the area of tissue surrounding the point of injection (or fluid withdrawal) which can interfere with the injection (or fluid withdrawal) process.

In a second technique, the barrel of a syringe device is provided with a noncollapsible slidable shield which can be manually moved backwardly about the barrel to expose the needle for a use whereafter the shield can be manually positioned forwardly about the barrel to shield the needle after the device has been used. See, for example, U.S. Pat. Nos. 4,898,590; 4,840,619; 4,816,022; 4,801,295; 4,758,231; 4,731,059. However, the shielding mechanism in this technique requires a procedure while the device is being used in this case manually moving the shield to the shielding position after the device has been used. Thus, if the operator forgets to perform this procedure, which can happen during a medical operation, for example, the needle remains unshielded and susceptible to accidental and potentially infectious contact by anyone working in the proximity of the needle.

In a third technique, a needle is retracted into the barrel of a syringe device after being used. See, for example, U.S. Pat. Nos. 4,861,338; 4,838,869; 4,838,863; 4,790,822; 4,747,831; 4,747,830; 4,675,005; 4,026,287. However, this technique too requires a procedure while the device is being used in this case dealing with activation of the retraction mechanism. If the operator forgets to perform this procedure, which can happen during a medical operation, for example, the needle remains exposed and susceptible to accidental and potentially infectious contact by anyone working in the proximity of the needle. There can also be the question of complicated fabrication, increased cost and complicated operation due to requirements of this technique, including that the needle itself be movable and that an actuation mechanism to retract the needle be provided.

SUMMARY OF THE INVENTION

One object of the present invention is to provide a syringe device with means for shielding a hypodermic needle attached thereto from accidental contact when the syringe device is not being used.

Another object of the present invention is to provide a means for automating a movable shield, integral with syringe member thereof, so as to normally bias the shield in the shielding position.

Another object of the present invention is to provide means for manually retracting a movable shield that is biased in a shielding position.

Another object of the present invention is to provide means for so retracting a movable shield that is biased in a shielding position that the needle is exposed prior to placement of needle against the skin surface (or vial surface) where injection (or fluid withdrawal) is to be made.

To achieve these and other objects, I have devised a syringe device in which I have made a movable shield member, integral with a syringe member of said device, to be movably interconnected with the syringe member for movement between a first position for shielding a needle member of said device and a second position for exposing the needle member, I have provided means for manually moving the shield member from the first to the second position, and I have disposed between the shield member and the syringe member, spring means for normally biasing the shield member in the shielding position when the syringe device is not being used.

DETAILED DESCRIPTION OF THE INVENTION

As shown in the drawing depicting an exaggerated, partially perspective, partially sectional view, a preferred embodiment of a syringe device 10 of the present invention comprises a syringe member 100, a movable shield member 200, a spring member 300, and a needle component 400.

Syringe member 100 defines in a first portion thereof a tubular body 110 forming a bore 112 on an inside surface for movably receiving a plunger 120 having a finger flange 130 provided at one end thereof. An opening 150 in tubular body 110 is formed in a second portion thereof for attachably receiving a hypodermic needle component 400 and allowing there to be fluid communication between a needle 410 of said component and bore 112. A finger flange 170 is provided at the opening of bore 112 for facilitating the movement of plunger 120 along bore 112 of syringe member 100.

Movable shield member 200 is a tubular body 210 having a finger flange 220 provided at one end thereof. Movable shield member 200 is fitted about syringe member 100 in a manner hereinafter described so as to be axially slidable with respect to the syringe member between a first position for shielding the hypodermic needle and a second position for exposing the needle.

Spring member 300 is provided along an outside surface of syringe member 100 between finger flange 170 of the syringe member and movable shield member 200 for normally urging the movable shield member forwardly along the syringe member to the shielding position wherein hypodermic needle 410 is shielded from accidental contact when syringe device 10 is not being used.

Needle component 400 comprises needle 410 and means for attaching the needle to syringe member 100 so that there is fluid communication between the needle and the syringe member.

Compression of spring member 300 in a manner hereinafter described causes the movable shield member to be urged backwardly to the second position so as to expose the needle for the desired use. Relaxation of the compressive force causes the spring member to restore the movable shield member forwardly of the hypodermic needle to the shielding position. Consequently, the spring loaded movable shield member provides means for normally biasing the shield member in the shielding position and for automatically restoring the movable shield member to the shielding position after the syringe device has been used.

In accordance with the invention, syringe member comprises a prior art syringe member modified as set forth below. Prior art syringe member comprises tubular body 110, bore 112, plunger 120 provided with finger flange 130 at one end thereof and a piston head 140 at another end thereof, opening 150, and finger flange 170. Tubular body 110 comprises polypropylene, glass, or other syringe suitable tubular body material. Bore 112 is smooth so as to provide a leak-proof slidable fit with piston head 140 of plunger 120, which is made from rubber or other syringe suitable piston material. Movement of the plunger inside bore 112 urges communication of fluid between syringe member and needle. Typical prior art syringe members (and prior art needle components 400) are described in the 1990 Catalog of "Sutures, Syringes and Needles, Scalpel Blades and Handles, Gloves" published by the Arista Surgical Supply Co., Inc. of New York, N.Y.

Modification of the prior art syringe member is effected about an outside surface thereof. Specifically, in lieu of a generally smooth tubular outer surface, the syringe member is provided with a retaining flange 180. Illustratively, the retaining flange is annular. Alternatively, the syringe member can be provided at intervals along its radius with one or more axially or otherwise oriented flanges sufficiently strong to provide the retaining means hereinafter described. As yet another alternative, one or more axial finger flanges can be so provided at intervals along the syringe radius as to angle outwardly in the finger flange 170 direction (i.e., so that an angle is formed between flange body and syringe member) thereby forming leaf springs which are biased towards an open position. This alternative allows a prefabricated movable shield member to ride, in the finger flange 170 direction, over the leaf spring, thereby facilitating the assembly of the shield member about the syringe member whereafter the free end of the leaf spring prevents the shield member from moving forwardly of the free end thereby providing retaining means as hereinafter described.

Retaining flange 180 comprises plastic, glass, or other syringe suitable material sufficiently strong to provide the retaining means hereinafter described. Preferably, a transparent material is used so that the contents of the syringe member and graduated markings on the outer surface thereof are visible throughout the retaining flange. Illustratively, the retaining flange is fabricated separately and attached to the tubular body by press fit, snap on, adhesive or other attachment means. Alternatively, the retaining flange is formed integral with the syringe member by molding techniques, for example.

Movable shield member 200 comprises a tubular body 210 made of plastic, glass or other syringe suitable material which is sufficiently strong to keep the needle from breaking therethrough. Preferably, the needle shielding end of the tubular body tapers inwardly so as to provide enhanced needle protection when the movable shield is in the needle protecting position. Alternatively, the shielding end can be formed in any shape so as to provide the needle protection desired.

Movable shield defines in a middle portion of its inside surface a bore 212. The bore receives syringe member 100 which cooperates with the wall of the bore in sliding engagement. A first and a second stepped bore 214, 216, respectively, formed along the inside surface of movable shield along plunger and needle end portions thereof, respectively, movably receive spring member 300 and retaining flange 180, respectively. Finger flange 220 is provided preferably at the plunger side of the movable shield for facilitating the movement of the shield along the syringe. The finger flange is preferably formed integral to the movable shield member when the movable shield member is in assembled form. Alternatively, the flange can be fabricated separately and attached to the movable shield by press fit, snap on, adhesive or other attachment means.

Preferably, the movable shield member is made from transparent material so that the contents of the syringe member and the graduated markings on the outer surface thereof are visible therethrough when the movable shield is disposed about the syringe. Alternatively, and regardless of the transparency of the shield member, a window can be defined therein for this purpose which can be further fitted with transparent syringe suitable material so as to enhance the strength and integrity of the movable shield while providing for the visibility properties previously described.

Illustratively, the movable shield is fabricated in parts and assembled by press fit, snap on, adhesive or other attachment means. Alternatively, the movable shield can be fabricated as a unitary piece using, for example, molding techniques.

Disposed about the syringe, the movable shield is held in place illustratively by prefabricated retaining flange 180 which is subsequently attached to the syringe as herein described. Alternatively, where retaining flange 180 is fabricated integral to the syringe member, the movable shield can be assembled about the syringe member. As yet another alternative, in a syringe member wherein retaining flange 180 is fabricated integral to the syringe member, leaf springs of the type previously described in connection with retaining flange 180 but which angle outwardly in the needle direction can be provided at intervals along the inside radius of the shield. This alternative allows a prefabricated shield to ride in the finger flange 170 direction over retaining flange 180 thereby facilitating the assembly of the shield member about the syringe member whereafter the free end of the leaf spring prevents the shield from moving forwardly of retaining flange 180 thereby providing retaining means as hereinafter described.

Assembled about the syringe, movable shield member 200 is adapted to move (using finger flange 220 as the reference point for this movement) between a first position A—A (or a position thereabout), the shielding position, and a second position, in the range B—B to C—C, wherein the needle is exposed. When the movable shield member is in the shielding position, a rear shoulder 217 of second step bore 216 of the movable shield member abuts the corresponding end face of retaining flange 180. Consequently, the flange portion and rear shoulder 217 of the second step bore cooperate to provide retaining means for keeping the shield from moving forwardly of the shielding position. When the movable shield member 200 is in position C—C, finger flange 220 of the movable shield member abuts the corresponding end face of finger flange 170 of syringe member 100.

Spring member 300 is a coiled spring disposed about the syringe member between finger flange 170 and shoulder 215 of first step bore 214 of movable shield member 200, which are adapted to seat opposite ends of the spring member. Alternatively, a spring of any shape and type and made from any elastic material can be used, as can other means for seating the spring, as hereinafter described.

Illustratively, the spring has an inner diameter of slightly greater than the outer diameter of the syringe member and need only be sufficiently strong to retract the shield and return it to its neutral position yet not so strong that the plunger begins to penetrate bore 112 of the syringe member before the shield is sufficiently retracted to expose the needle. Preferably, the spring member is such that the plunger does not penetrate the bore until after the movable shield is in the C—C position, However, stronger springs which allow the plunger to penetrate once the shield enters the range of position B—B to C—C or which causes plunger penetration before needle exposure can also be used. The action of spring member 300 urges movable shield member 200 forwardly along the syringe member 100 so as to protect hypodermic needle 410 when the syringe device is not being used.

Illustratively, in a Becton, Dickinson and Company 10 cc, 20G1 syringe with detachable needle, item No. SYR 1-31, manufacturer No. 9644, starting at about 6.985 cm (2.75 inch) from finger flange 170 and extending toward the finger flange is defined from 1.5875 cm (⅝ inch) inner diameter 0.3175 cm (4/32 inch) wall thickness, PVC reinforced PVC, (manufactured separately from the syringe and tightly slipped thereon), a retaining flange 180 having a length of about 0.9525 cm (12/32 inch). Slidably disposed about the syringe member, starting, when in the shielding position, at about 1.905 cm (¾ inch) from finger flange 170 and extending toward the needle, is a movable shield member 200 comprising a 2.54 cm (1 inch) inner diameter, 0.3175 cm (4/32 inch) wall thickness, first acrylic tubular member having a length of about 12.065 cm (4-24/32 inch) in which is tightly fitted so that an end portion terminating on the needle side thereof abuts flange 180, a 1.905 cm (¾ inch) inner diameter, 0.3175 cm (4/32 inch) wall thickness, second acrylic tubular member having a length of about 2.2225 cm (28/32) inch. In this example, the inside surface of the second acrylic tubular member forms bore 212 with the inside surfaces of the first acrylic tubular member on both ends of the bore forming outwardly stepped bores 214, 216. Disposed about the syringe member between finger flange 170 of syringe member 100 and the second acrylic tubular member of the movable shield member is spring member 300 comprising a No. 156 compression spring manufactured by the Select-A-Spring-Corp. of Bayonne, N.J. A 1.27 cm (16/32 inch) inner diameter, 0.635 cm (8/32 inch) long tubular member made of syringe suitable piston head material having an outer diameter of about 1.429 cm (18/32 inch) is disposed about the piston head of the plunger so as to sufficiently increase the piston-to-bore resistance of the cylinder head-to-bore slidable fit so that the plunger does not penetrate the bore until the spring has allowed the movable shield to be retracted to about the C—C position.

The syringe device is finally assembled in the following manner. Spring member 300 is disposed about syringe member 100. The second acrylic tubing is slipped over syringe member 100. Retaining flange 180 is then tightly slipped over the syringe so as to terminate from finger flange 170 as previously indicated thereby keeping the second acrylic tubing from extending forwardly thereof. The first acrylic tubing of the movable shield member is then disposed about the syringe member by tightly slipping it into place over the second acrylic tubing so that when in the shielding position, starting at about 1.905 cm (¾ inch) from finger flange 170, it extends away therefrom.

In the normal or shielding position illustrated in the drawing, spring member 300 biases the movable shield member forwardly along the syringe member so that shoulder 217 formed by stepped bore 216 abuts retaining flange 180. An injection task using syringe member 100 is accomplished in one illustrative manner by initially applying force at a first level across finger flanges 220 and 130 of the movable shield member and plunger, respectively, which acts to bias the movable shield member toward finger flange 170 of the syringe member. Opposing the movement of the movable shield member is spring member 300. Consequently, force at a first predetermined value will cause the movable shield member to move relative to the syringe member from the shielding position A—A to the C—C position to expose hypodermic needle 410. With the needle exposed, the needle can be placed against the injection surface and then forced therethrough so as to enter the patient.

Continued force increases the force across finger flanges 220 and 130 to a second higher predetermined force whereby plunger 120 is urged to penetrate the bore. In this manner, the injection task of communicating fluid contained in the syringe through the needle is accomplished.

Upon relaxation of force across finger flanges 220 and 130 of the movable shield member and plunger, respectively, the force biasing the movable shield member 200 toward finger flange 170 is reduced causing the restoring force of the spring member 300 to move the movable shield member 300 in a direction from position C—C to position A—A. Eventually, movable shield member 200 is biased via spring member 300 to the position illustrated in the drawing wherein shoulder 217 of the movable shield member is abutting retaining flange 180. In this neutral position, the movable shield member shields the hypodermic needle when the syringe device is not being used.

The task of withdrawing a fluid from a vial, for example, into the syringe member is illustratively accomplished by initially applying a force across finger flanges 170 and 220 causing the movable shield member to be urged backwardly to expose the needle whereupon the needle can be inserted into the vial and the plunger drawn outwardly within the barrel with the other hand to accomplish the fluid withdrawal task. Relaxation of the force across the respective finger flanges when the syringe device is through being used causes the spring member to restore the movable shield member forwardly of the hypodermic needle of the syringe device. Consequently, the spring loaded movable shield member provides means for automatically restoring the movable shield member to protect the hypodermic needle of the syringe device when the syringe device is not being used.

It will be appreciated that where so hard a spring is used that the plunger is allowed to penetrate the bore before the needle is exposed, the injection task can be illustratively accomplished by retracting, by applying force across flanges 170 and 220, and holding the shield member in the retracted position with one hand after which the plunger can be urged into the bore with the other hand.

It will also be appreciated that other retaining means can be provided to the syringe device for retaining the movable shield member from moving forwardly of the shielding position. For example, an annular recess (or narrow recesses, such as grooves, which are axial or angled to or about the longitudinal axis of the syringe member) can be defined on an outer surface of the syringe member for movably receiving bore 212 (or one or more flanges defined on the inside surface of the shielding member). Retaining means here is provided by abutment of shoulder 217 of second stepped bore 216 (or of such one or more flanges defined on the inside surface of the shielding member, as the case may be) against an end wall of the recess terminating on the needle side of the syringe member. The recesses can also be such as to receive spring member 300. With an annular recess, for example, the spring member can be disposed between shoulder 215 of first step bore 214 and an end wall of the recess terminating on the finger flange 170 side of the syringe member. Off-axis grooves can also be used to introduce some off-axial movement into the shield as the flanges of the shield are caused to ride such grooves between shielding and non-shielding positions.

It will be further appreciated that although movable shield member is described in terms of a tubular body, any structure which accomplishes the shielding objective herein described can be used As one example, shielding member can comprise a first tubular region disposed about the syringe member near finger flange 170, having a finger flange 220 and having a bore 212 and stepped bores 214, 216 defined therein, and a second tubular region extending between positions D—D and E—E shown in the drawing (when the shield is in the shielding position) but with the region therebetween comprising, instead of a tubular member, one or more axial struts connecting the first tubular region to the second tubular region. The struts maintain the two tubular regions in a fixed spatial relationship with respect to each other and openings between the struts provide for the visibility properties previously described. In this embodiment, the first tubular region and/or the struts are in such firm yet slidable contact with the syringe member as to keep the shielding member from wobbling about the syringe member when the device is being used—a desirable feature for any embodiment of the present invention. As another example, a noncylindrical structure which accomplishes the shielding objective herein described can be used.

It will be yet further appreciated from the drawing, where movable shield member forms an outer surface of the syringe device, that the syringe device can in fact be so fabricated that the movable shield is substantially incorporated within the syringe member. As one example, the device shown in the drawing can be so provided with a cylindrical body, disposed about the movable shield member so as to allow the shield member to be movable thereagainst and attached at a finger flange 170 end thereof to a midsection of finger flange 170 of the syringe device, and provided further with an elongate opening for finger flange 220 of the shield member to extend therethrough for movement of the shield member between A—A and C—C positions, as to be said to substantially incorporate the movable shield while allowing said shield to be movable between shielding and exposing positions.

Moreover, it will be appreciated that other varying permutations and combinations for dimensioning of the movable shield member, spring member and syringe member can be used so as to provide a desired shielding to the syringe device.

While the invention has been described in conjunction with specific embodiments, it is evident that numerous alternatives, modifications, and variations will be apparent to those skilled in the art within the spirit and scope of the invention described above.

I claim:

1. A syringe device comprising:
    a syringe member provided with a hypodermic needle;
    a movable shield member movably interconnected with said syringe member for movement between a first position for shielding the hypodermic needle and a second position for exposing the hypodermic needle;
    means for manually moving the shield member from the first to the second position; and
    biasing means disposed between said syringe member and said movable shield member for normally biasing the movable shield in the shielding position;
    wherein said movable interconnecting of said movable shield member with said syringe member comprises a means for retaining the shield member from moving forwardly of the shielding position, said retaining means comprising at least one flange provided along an outside surface of the syringe member and a bore provided with an outwardly stepped bore defined along an inside surface of said shield member, said stepped bore movably receiving said flange member so that a shoulder portion of said stepped bore abuts a corresponding end portion of said flange member when said shield member is in the shielding position.

2. The device of claim 1 wherein said flange comprises an annular flange.

3. The device of claim 1 wherein said flange comprises a leaf spring.

4. The device of claim 1 wherein said biasing means comprises a coiled spring.

5. The device of claim 1 wherein said manually moving means comprises a first finger flange on said syringe member and a second finger flange on said movable shield member for urging the biasing means to expose the needle.

6. The device of claim 3 wherein said leaf spring angle outwardly in the finger flange direction.

7. A syringe device comprising:
a syringe member provided with a hypodermic needle;
a movable shield member movably interconnected with said syringe member for movement between a first position for shielding the hypodermic needle and a second position for exposing the hypodermic needle;
means for manually moving the shield member from the first to the second position; and
biasing means disposed between said syringe member and said movable shield member for normally biasing the movable shield in the shielding position;
wherein said movable interconnection of said movable shield member with said syringe member comprises a means for retaining the shield member from moving forwardly of the shielding position, said retaining means comprising a recess defined within an outside surface of said syringe member, and at least one flange provided along an inside surface of said shield member, said recess movably receiving said flange member so that a shoulder portion of said flange member abuts a corresponding end portion of said recess when said shield member is in the shielding position.

8. The device of claim 7 wherein said flange comprises a leaf spring.

9. The device of claim 7 wherein said recess comprises an annular recess.

10. The device of claim 7 wherein said biasing means comprises a coiled spring.

11. The device of claim 7 wherein said manually moving means comprises a first finger flange on said syringe member and a second finger flange on said movable shield member for urging the biasing means to expose the needle.

12. The device of claim 7 wherein said recess comprises an annular recess and said biasing means comprises a coiled spring received by said recess.

13. The device of claim 8 wherein said leaf spring angles outwardly in the needle direction.

* * * * *